United States Patent
Kotsos et al.

(10) Patent No.: US 10,322,225 B2
(45) Date of Patent: *Jun. 18, 2019

(54) SYSTEM AND METHOD OF MONITORING BLOOD LEAKS DURING HEMODIALYSIS THERAPY EMPLOYING WIRELESS COMMUNICATION

(71) Applicant: Fresenius Medical Care Holdings, Inc., Waltham, MA (US)

(72) Inventors: Michael Emmanuel Kotsos, Concord, CA (US); Alexander J. Brown, Concord, CA (US); Roland Levin, Concord, CA (US); Fei Wang, Concord, CA (US); Donovan Halliburton, Concord, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 227 days.

This patent is subject to a terminal disclaimer.

(21) Appl. No.: 15/381,810

(22) Filed: Dec. 16, 2016

(65) Prior Publication Data
US 2017/0112994 A1 Apr. 27, 2017

Related U.S. Application Data

(63) Continuation of application No. 13/829,868, filed on Mar. 14, 2013, now Pat. No. 9,555,178.
(Continued)

(51) Int. Cl.
*A61M 1/16* (2006.01)
*A61M 1/36* (2006.01)
(Continued)

(52) U.S. Cl.
CPC ........ *A61M 1/3656* (2014.02); *A61M 1/1601* (2014.02); *A61M 1/267* (2014.02);
(Continued)

(58) Field of Classification Search
CPC .. A61M 1/3656; A61M 1/267; A61M 1/1601; A61M 2205/50;
(Continued)

(56) References Cited

U.S. PATENT DOCUMENTS 7,492,842 B2   2/2009  Yen et al.
7,605,710 B2  10/2009  Crnkovich et al.
(Continued)

FOREIGN PATENT DOCUMENTS

EP        1 315 313       5/2003
WO    WO 2005/107580    11/2005

OTHER PUBLICATIONS

Cover Letter with proposed claim language from Applicant's representative; Ronald Demscher; Jan. 31, 2019 (Year: 2019).*
(Continued)

*Primary Examiner* — Joseph W Drodge
(74) *Attorney, Agent, or Firm* — Hamilton, Brook, Smith & Reynolds, P.C.

(57) ABSTRACT

According to at least one example embodiment, a system of monitoring blood leaks during hemodialysis therapy includes a wetness sensing device and a hemodialysis machine. The wetness sensing device is configured to transmit information wirelessly, the information being indicative of an absence of a liquid or a presence of a liquid. The hemodialysis machine includes, or is coupled to, a wireless receiver having two or more antennas. Signals received at the two or more antennas are decoded at the wireless receiver. If decoded signals indicate a detected wetness, the hemodialysis machine is caused to halt blood flow in and out of the machine and generate an alarm.

27 Claims, 10 Drawing Sheets

Related U.S. Application Data

(60) Provisional application No. 61/746,859, filed on Dec. 28, 2012.

(51) Int. Cl.
  *B01D 61/30*  (2006.01)
  *G08B 21/20*  (2006.01)
  *G16H 40/63*  (2018.01)
  *G06F 19/00*  (2018.01)
  *H04B 7/08*   (2006.01)
  *A61M 1/26*   (2006.01)

(52) U.S. Cl.
  CPC ............ *B01D 61/30* (2013.01); *G06F 19/00* (2013.01); *G08B 21/20* (2013.01); *G16H 40/63* (2018.01); *H04B 7/08* (2013.01); *H04B 7/0882* (2013.01); *A61M 2205/15* (2013.01); *A61M 2205/3561* (2013.01); *A61M 2205/3592* (2013.01); *A61M 2205/50* (2013.01)

(58) Field of Classification Search
  CPC .. A61M 2205/3592; A61M 2205/3561; A61M 2205/15; A61M 2205/3562; A61M 1/16; G06F 19/00; G16H 40/63; B01D 61/30; B01D 61/32; B01D 2311/24; B01D 2311/243; H04B 7/0882; H04B 7/08; H04B 7/0885; G08B 21/20
  USPC .... 210/85, 646; 604/371, 4.01–6.11, 11, 65; 340/604, 605, 640; 600/371
  See application file for complete search history.

(56) References Cited

U.S. PATENT DOCUMENTS

| | | | |
|---|---|---|---|
| 7,973,667 | B2 | 7/2011 | Crnkovich et al. |
| 8,216,173 | B2 | 7/2012 | Dacey |
| 9,555,178 | B2* | 1/2017 | Kotsos ............... H04B 7/08 |
| 2003/0128125 | A1 | 7/2003 | Burbank |
| 2004/0152953 | A1 | 8/2004 | Goedeke |
| 2004/0214532 | A1 | 10/2004 | Azuma |
| 2006/0195162 | A1 | 8/2006 | Arx et al. |
| 2008/0041792 | A1* | 2/2008 | Crnkovich ............ A61F 13/42 |
| | | | 210/739 |
| 2009/0082649 | A1 | 3/2009 | Muller et al. |
| 2009/0131858 | A1* | 5/2009 | Fissell ................ B01D 61/145 |
| | | | 604/57 |
| 2010/0100026 | A1 | 4/2010 | Morris |
| 2013/0018440 | A1 | 1/2013 | Chow et al. |
| 2013/0145429 | A1 | 6/2013 | Mendel |
| 2013/0253612 | A1 | 9/2013 | Chow |
| 2014/0155098 | A1 | 6/2014 | Markham et al. |

OTHER PUBLICATIONS

Proposed claim language from Applicant's representative, Ronald Demscher; Jan. 31, 2019 (Year: 2019).*

International Search Report and Written Opinion of PCT/US2013/077014 dated May 23, 2014, entitled "System and Method of Monitoring Blood Leaks During Hemodialysis Therapy Employing Wireless Communication".

International Preliminary Report on Patentability of PCT/US2013/077014 dated Jul. 0, 2015, entitled "System and Method of Monitoring Blood Leaks During Hemodialysis Therapy Employing Wireless Communication".

Toba, et al., "Wireless Moisture Sensor Using a Microstrip Antenna", Journal of Sensors, vol. 2011, Article ID 827969, 6 pages (2011).

* cited by examiner ative application. No. 13/829,868, filed Mar. 14, 2013, which claims the benefit of U.S. Provisional Application No. 61/746,859, filed on Dec. 28, 2012. The entire teachings of the above application are incorporated herein by reference.

BACKGROUND OF THE INVENTION

During hemodialysis treatment, there is a risk that venous access may become dislodged. In the case that such event goes unnoticed, arterial access continues to draw blood from the patient while the dislodged venous access does not return blood to the patient, which may quickly cause the patient to bleed out and even bleed to death. Wetness detector devices present a viable solution for efficiently and timely detecting blood leaks.

SUMMARY OF THE INVENTION

According to at least one embodiment, a system of monitoring blood leaks during hemodialysis therapy includes a wetness sensing system and a hemodialysis machine. The wetness sensing system is configured to transmit information wirelessly, where the information is indicative of an absence of a liquid or a presence of a liquid. The hemodialysis machine includes, or is coupled to, a wireless receiver having two or more antennas. Signals received at the two or more antennas are decoded at the wireless receiver. If decoded signals indicate a detected wetness, the hemodialysis machine is caused to halt blood flow in and out of the machine and generate an alarm.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
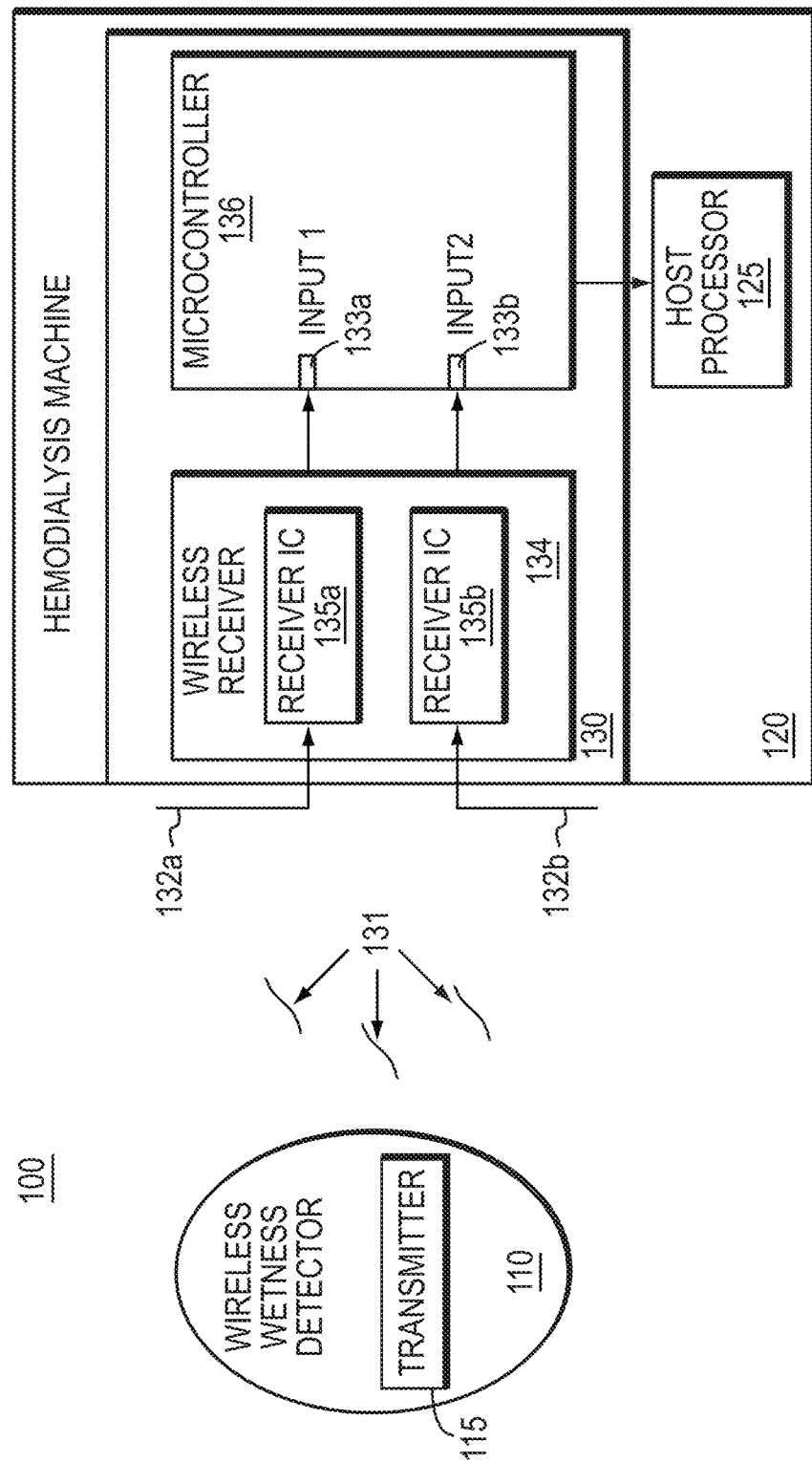
FIG. 1 is a block diagram of a system of monitoring blood leaks during hemodialysis therapy, according to at least one embodiment.

A description of example embodiments of the invention follows.

The teachings of U.S. Pat. No. 7,605,710 are herein incorporated by reference in their entirety.

Embodiments generally relate to wireless wetness detection. Detecting the presence of wetness and/or liquid leaks have a number of applications including detecting blood leaks or other liquid line leaks during procedures that involve the removal of blood from a person, procedures such as blood donation, blood detoxification, blood filtration/hemofiltration and hemodialysis. In hemodialysis for example, blood is removed from a patient through a needle into a blood liquid line circuit that carries the blood to a hemodialysis machine that filters out waste toxins and removes excess water from the blood. Dislodgement of the needle or a break in the blood liquid line leads to rapid and potentially fatal blood loss because blood is normally removed from the patient and through the blood liquid line circuit at a rapid rate. For this reason, hemodialysis, which generally takes several hours and must be performed several times per week, is typically done in a medical setting where patients can be supervised. Patients may be monitored visually by medical personnel for blood leaks so that, if needle displacement occurs, the leak can be identified and remedied before detrimental blood loss takes place.

According to an embodiment, Wireless Wetness Detectors (WWDs) can be used to make this monitoring process a simpler task. A WWD can monitor for wetness, such as a blood leak and trigger an alert when such a leak occurs. In the case of hemodialysis, automated monitoring frees medical personnel from having to inspect a number of patients visually for blood leaks due to needle displacement or blood line breaks, allowing the medical personnel to focus on other tasks.

In some examples, WWDs are battery powered wireless devices that include a wetness sensor, a microcontroller with an internal radio frequency (RF) amplifier, and an antenna. During dialysis therapy (e.g., a hemodialysis therapy session), a WWD device, that may be rigid or flexible, is placed on top, or in the vicinity, of a patient's vascular access point. The WWD device actively communicates with a wirelessly tethered hemodialysis machine during treatment. Example embodiments of WWDs that may be employed in embodiments are discussed hereinbelow in relation to FIGS. 7-10.

When the WWD device senses wetness, e.g., during a blood leak, the WWD device notifies the hemodialysis machine, which responds with a blood leak alarm. The hemodialysis machine also stops the flow of blood to and from the patient. However, in some examples, if the wireless connection were to become disabled or interrupted (e.g. "drop out"), the hemodialysis machine would not be notified of the blood leak, resulting in an unintended blood loss from the patient.

In some examples, the reliability of a wireless communication may be limited by effects of interference on the RF signal that are caused by the surrounding environment. This effect is known as multipath induced fading. In a scenario with multipath induced fading, a transmitted signal is reflected from multiple surfaces and is recombined with phase offsets at a receiver antenna. If the phase offsets of the signals at the receiver antenna are an odd multiple of 180°, known as a deep fade, the resulting signal power is significantly reduced.

In some examples, the wireless signal linking a WWD device and a hemodialysis machine may be susceptible to multipath fading and communication drop outs. Such potential failures, e.g., wireless communication drop outs, represent a significant inconvenience since a potential failure coinciding with a blood leak during a hemodialysis therapy session may put a patient's health or life at risk.

In an embodiment, a system of monitoring blood leaks having a wireless receiver system employs spatial antenna diversity. The wireless receiver system includes two or more physically separated antennas. For example, in a scenario where a first antenna is losing information due to multipath induced fading, other available antenna(s) may receive the signal if sufficiently separated from the first antenna. In the following description, improvements to the WWD device enhancing respective reliability are presented.

FIG. 1 is a block diagram that shows a system 100 of monitoring blood leaks during hemodialysis therapy, according to at least one embodiment. The system 100 includes a WWD device 110 equipped with a wireless transmitter 115 and a hemodialysis machine 120 coupled to a multi-antenna wireless receiver device 130. In an embodiment, the WWD 110 is a rigid device configured to be placed in the vicinity of a patient's vascular access point. In yet another embodiment, the WWD 110 is the flexible WWD 710 or 1010 described hereinbelow in relation to FIGS. 7 and 10 respectively. According to some examples (such as the example shown in FIG. 1), the multi-antenna wireless receiver device, or system, 130 may be a component implemented within the hemodialysis machine 120. Alternatively, the multi-antenna wireless receiver device 130 may also be a separate device coupled to the hemodialysis machine 120 through a communications link. The multi-antenna wireless receiver device 130 includes, for example, two or more antennas, e.g., 132a and 132b, a receiver module 134, and a microcontroller 136. The receiver module 134 may include a single RF receiver circuit or, alternatively, two or more RF receiver circuits, such as receiver circuit 135a and receiver circuit 135b, each being associated with a respective antenna, e.g., 132a and 132b.

The multi-antenna wireless receiver system 130 may be implemented as a printed circuit board with the two or more antennas, e.g., 132a and 132b, coupled thereto. Within the printed circuit board, the receiver module 134 may be implemented as RF receiver electronics, which directly interface to a microcontroller 136. The RF receiver electronics include, for example, an analog-to-digital converter (not shown). The RF receiver electronics may further include electronics hardware (not shown) configured to demodulate received RF signals 131.

The microcontroller 136 is configured to receive data streams, associated with the RF signals 131 received at the two or more antennas, e.g., 132a and 132b, and process and analyze multiple data streams to output data selectively that indicates whether a wetness condition has been detected at the patient's vascular access point.

Existing wireless systems in the art employing antenna diversity usually switch between the multiple available antennas based on a calculated error rate or measured RF power at each antenna. In other words, in existing systems, only one antenna is being used at a given point in time and, as such, valuable information from unused antenna(s) may be overlooked or missed. According to at least one embodiment, multiple data streams associated with RF signals received at the two or more antennas, e.g., 132a and 132b, are continuously monitored at the microcontroller 136 in order to decode signals sent from the WWD device 110 correctly. Since data from all antennas is continuously monitored, no data is lost or ignored due to antenna switching. The multi-antenna wireless receiver system 130 prevents the wetness detection information from being lost and allows a hemodialysis machine to respond quickly to a blood leak.

In the system 100, the WWD device 110 transmits, via a coupled transmitter 115, a signal, e.g., a message including a flag indicative of whether or not a wetness condition is detected, which is received by the two or more separate antennas, e.g., 132a and 132b. Signals received by the two or more separate antennas, e.g., 132a and 132b, are routed to the receiver module 134, which includes one or more receiver integrated circuits (IC), e.g., 135a and 135b, to demodulate the RF signals, optionally independently, to corresponding logic level digital signals. The microcontroller 136 reads and samples the information of the digital signals, e.g, 133a and 133b, from the one or more receiver ICs, e.g., 135a and 135b, e.g., simultaneously, and performs digital signal processing and decision making. Information decoded by the microcontroller 136 is sent, e.g., from a universal asynchronous receiver transmitter (UART) port, serially to a host processor 125. The host processor 125 may be, for example, associated with a functional circuit board (not shown) within the hemodialysis machine 120. The host processor 125 is configured to cause display of a message to a user of the hemodialysis machine 120 and provide input data, indicative of whether or not wetness is detected, to one or more safety system controls associated with the hemodialysis machine 120. The host processor 125 may, for example, cause an alarm, such as the audible alarm associated with the alarm device 330 described herein, to be activated.

According to at least one embodiment, the message data received from the WWD device 110 is in the form of pulse width modulation (PWM) signals. Decoded PWM signals are sent to one or more hardware UARTs, where bits are converted into bytes to be read by the host processor 125. The one or more hardware UARTs are, for example, built into the microcontroller 136. The use of the hardware UART in the microcontroller 136 saves CPU cycles that would otherwise be needed to assemble the message bytes. Software in the microcontroller 136 reads the data from different channels and stores the respective data in a separate array for each channel. When enough bytes are received to complete an entire message, the message bytes for each channel are checked against a cyclic redundancy check (CRC)/check sum that is part of the message to determine which of receiver channels has received authenticated data. If the message from either channel is correct, the message is forwarded on for further processing by the host processor 125. If both channels receive a correct message with a correct check sum at the same time, one message is ignored to prevent duplicate message processing. Correctness or authenticity of messages may be verified using, for example, a CRC. For example, a check sum may be calculated for each received message to determine whether or not the data in the message was changed. Changes to the data during transmission, for example, render the message inauthentic.

The two or more antennas, e.g., 132a and 132b, may be placed at any angle relative to each other, as long as they are separated by a distance, e.g., distance between their centers, larger than or equal to the operating wavelength divided by four. For example, the two antennas 132a and 132b may be oriented 180 degrees relative to each other by means of a simple, easy to manufacture molded plastic holder. The holder allows the antennas to be mounted in the desired orientation. An antenna clip designed for ease of use and durability may be employed. The implementation may be designed for field upgradeability.

According to at least one embodiment, digital signal processing or decision making are performed through executable software. Software instructions may be used in performing (1) filtering to remove unwanted spurious signals, e.g., glitches, sometimes referred to as signal spikes, (2) continuous monitoring of simultaneous data streams, and (3) decision making in validating authenticity of data.

The WWD device 110 may use On-Off Keyed (OOK) or Amplitude Shift Keyed (ASK) RF modulation formats, which are typically used to conserve power in a battery powered transmitter, or other modulation formats, such as a Quadrature Phase Shift Keying (QPSK) format or the like. The resulting transmitted wave is a PWM signal. The use of pulse width modulation of the data ensures that the total "on" time of the transmitter is close to 50% of data unit, e.g., a bit, duration. Keeping the transmitter 115 of the WWD device 110 "on" close to 50% of a bit time duration helps an automatic gain control circuit on the RF receiver adjust to the signal level. In the one or more receiver ICs, e.g., 135a and 135b, the gain control circuit uses the 50% power point in determining the threshold for a "1" or a "0." During the reception of a signal, the output of the OOK demodulating receiver is a PWM signal, with added glitches due to noise and multipath induced fading.

The input PWM signals, e.g., 133a and 133b, include strings of binary 0's and 1's. A symbol 0 is, for example, encoded as 33% high, whereas a symbol 1 is encoded as 66% logic high. When a RF receiver converts the RF signal into a digital output, some glitches may be present. The glitches present in these waveforms are defined as inadvertent low or high transitions that are less than 33% of the total bit period. Implementations of PWM decoders known in the art usually do not have the functionality to handle cases where these glitches exist, and may misinterpret the intended value of the received bit.

According to at least one embodiment, the microcontroller 136 includes a PWM decoder that uses a continuous monitoring window to remove the effect of the unwanted glitches in the received bit streams from all available receiver channels. The PWM decoder is, for example, implemented as software. Another implementation could be executed in a field-programmable gate array (FPGA). The PWM decoder samples the PWM input at a rate much higher than the bit rate, e.g., at sixteen or more samples per bit. The PWM decoder stores the samples in a circular buffer whose total size equals the number of samples per bit period. A running sum of the circular buffer is calculated after every sample is recorded. When the sum calculated is greater than 50% of the number of samples in one period, a logic high is output for the respective bit. If the sum is less than 50%, a logic low is output for the respective bit. Thus, as long as the distortion of the PWM signal does not result in the total PWM data high time crossing the 50% threshold, the data will be correctly decoded.

Figure 2:
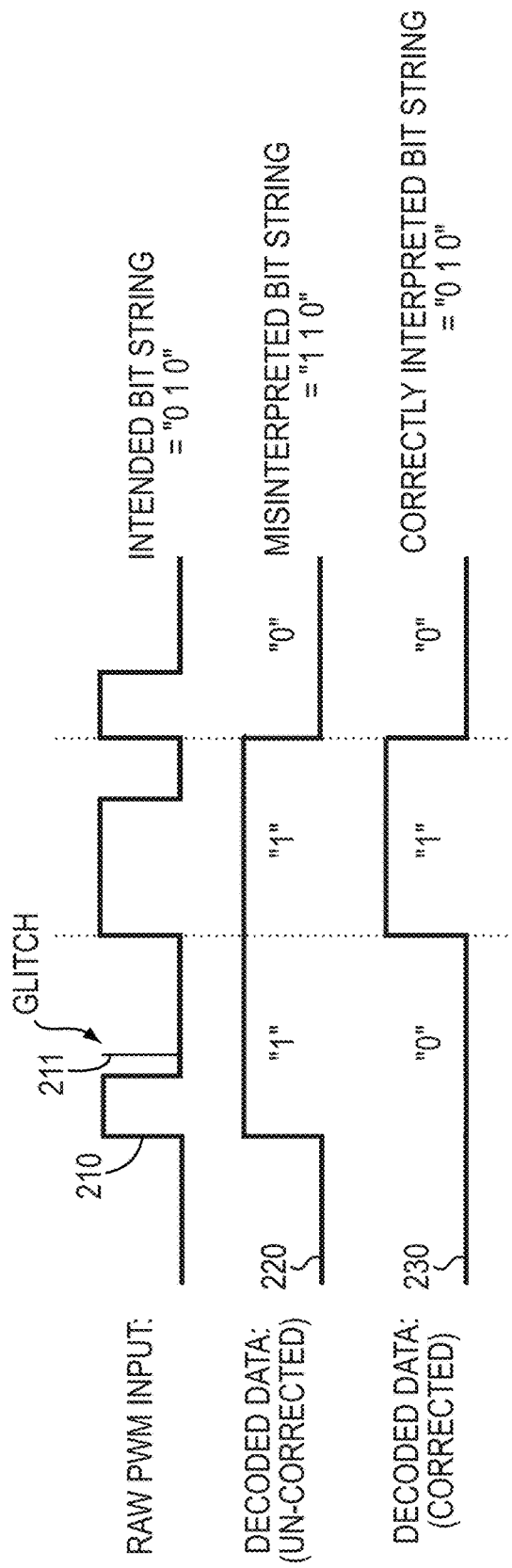
FIG. 2 is a timing diagram that illustrates example decoding of a pulse width modulation (PWM) bit stream that contains a glitch in one of the bits.

FIG. 2 shows example decoding of a PWM bit stream 210 that contains a glitch 211. The input PWM bit stream 210 includes the glitch 211 at the first bit. A first decoded data signal 220 indicates how the PWM input bit stream 210 may be misinterpreted due to the presence of the glitch 211. A second decoded data signal 230, which represents a bit stream decoded by calculating a running sum of the circular buffer after every sample, is recorded. Since the PWM data glitch 211 does not result in the total high time crossing the 50% threshold, the glitch does not impact the decoded data. Taking many samples of the PWM data per bit time allows the PWM decoder to look at the data in small pieces and thus prevents a small disturbance in the PWM data from impacting the output.

Figure 3:
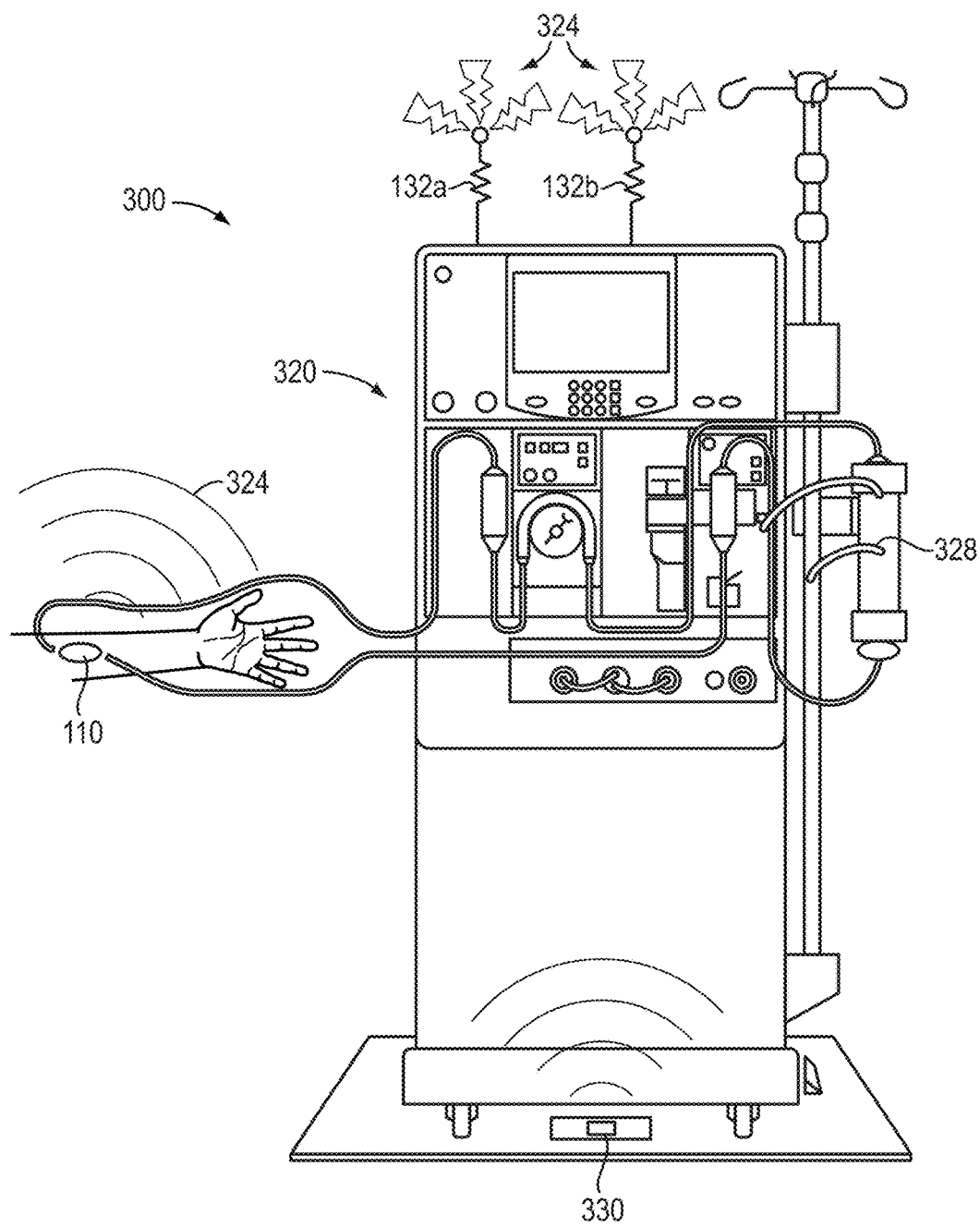
FIG. 3 is a schematic diagram illustrating a wetness detector system in which an example embodiment may be implemented.

An embodiment of the system 100 may be integrated into a hemodialysis system, such as the system 300 depicted in FIG. 3. The system 300 includes a WWD 110 attached to a wound dressing covering a needle insertion site. The WWD 110 may embody the WWD 710 described hereinbelow. A signal 324 of a blood leak is transmitted via two or more antennas, e.g., 132a and 132b, either wirelessly or through wires 328, to a receiver unit integrated with the hemodialysis treatment operation unit 320. In this depicted system 300, transmission of a blood leak triggers an audible alarm that emanates from an alarm device 330 (e.g., a speaker) located beneath the hemodialysis operation unit 320. The hemodialysis treatment operation unit 320 may be configured to stop blood pumps to protect any further blood leaks. The hemodialysis treatment operation unit 320 may incorporate, and couple thereto multiple antennas, e.g., 132a and 132b, wireless receiver system 130, with wireless receiver module 134, associated receiver circuits, e.g., 135a and 135b, and microcontroller 136, as well as host processor 125.

Figure 4:
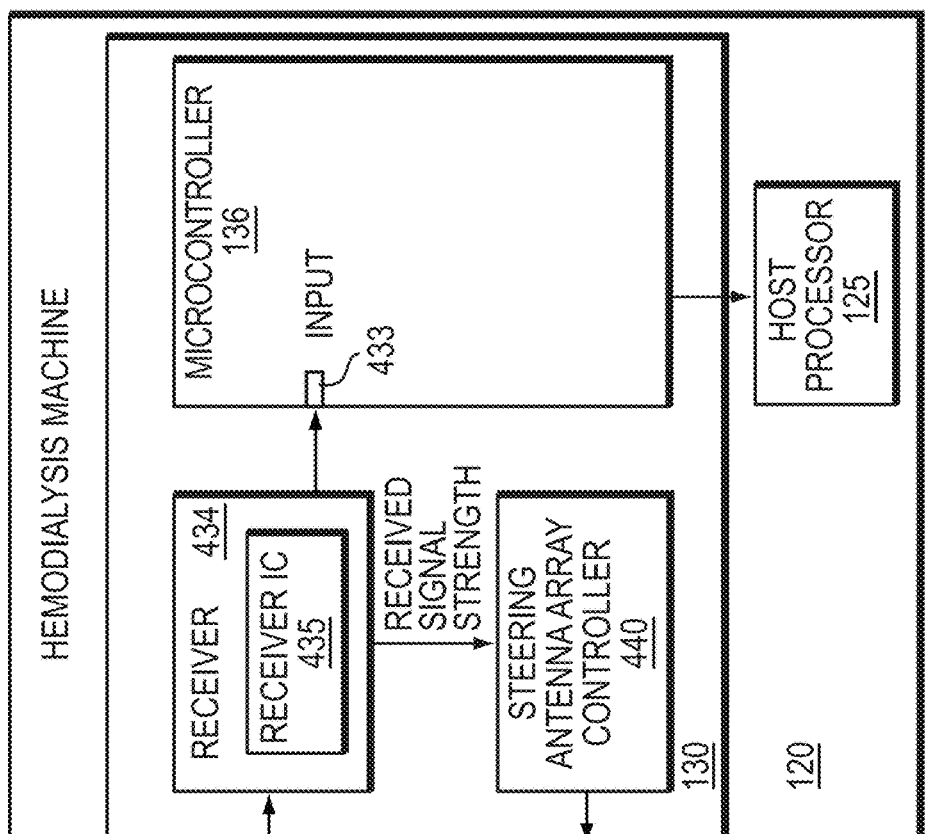
FIG. 4 is a block diagram of a system of monitoring blood leaks during hemodialysis therapy using a steering antenna array.
Figure 4:
Figure 4:
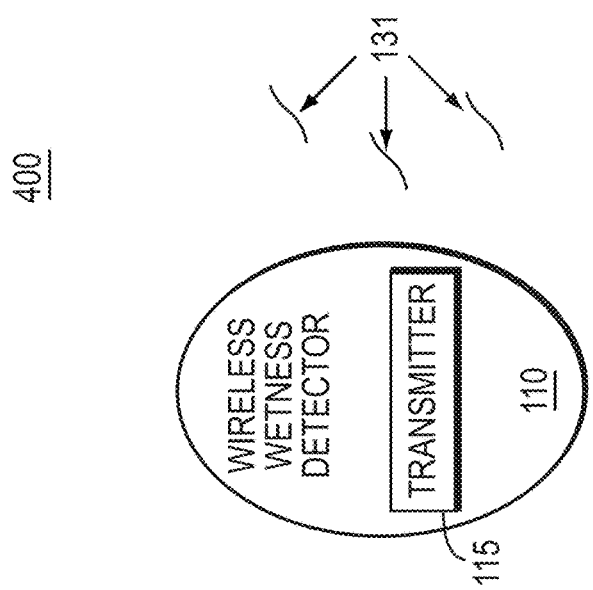

FIG. 4 depicts a block diagram of a system 400 for monitoring blood leaks during hemodialysis therapy, according to at least one embodiment. The system 400 includes a WWD 110 with its coupled transmitter 115. The system 400 includes a hemodialysis machine 120 coupled to a wireless receiver device 130 and a host processor 125. The receiver device 130 includes, for example, a steering antenna array 432, a receiver module 434, which may include RF receiver circuit 435, a steering antenna array controller 440 and a microcontroller 136.

In the system 400, the WWD 110 transmits, via a transmitter 115, a message including a flag indicative of whether or not a wetness condition is detected. This message is received by the steering antenna array 432. Signals received at the steering antenna array 432 are routed to the receiver module 434, which includes one or more receiver integrated circuits, e.g., the receiver circuit 435. The receiver integrated circuit 435 may demodulate the RF signals to corresponding logic level digital signals. From the receiver module 434, received signal strength is determined, and this information is routed to the steering antenna array controller 440. The steering antenna array controller 440 is configured to optimize the steering antenna array 432, based upon the received signal strength information. Upon receiving signal strength information from the receiver module 434, the steering antenna array controller 440 controls the steering antenna array 432 in order to optimize the received signal strength at the steering antenna array 432. From the receiver module 434, signals are routed to the input 433 of the microcontroller 136. The microcontroller 136 reads and samples the information of the digital signal and performs digital signal processing and decision making.

Information decoded by the microcontroller 136 is sent, e.g., from a UART port, serially to a host processor 125. The host processor 125 may be, for example, associated with a functional board within the hemodialysis machine 120. The host processor 125 is configured to cause display of a message to a user of the hemodialysis machine 120 and provide input data, indicative of whether or not wetness is detected, to safety system controls associated with the hemodialysis machine 110. The host processor 125 may, for example, cause an alarm, such as the alarm 330, to be activated.

Figure 5A:
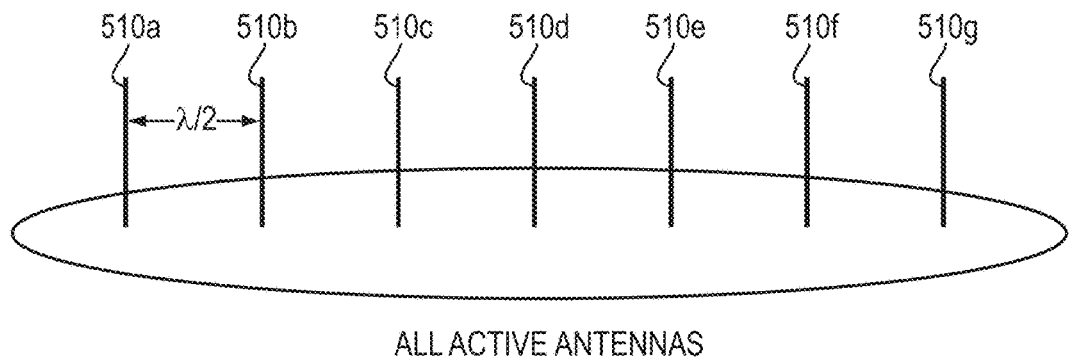
FIG. 5A is a simplified diagram of a linear steering antenna array.

FIG. 5A is a simplified diagram of an all-active linear steering antenna array 500a. The linear steering antenna array 500a may be implemented in the system 400 as the steering antenna array 432. The linear steering array 500a includes active antennas 510a-510g. The active antennas 510a-510g may be separated a half wavelength distance, as depicted in FIG. 5a as λ/2, to ensure proper inductive coupling. The linear steering antenna array 500a may be operated in a manner as is known in the art.

Figure 5B:
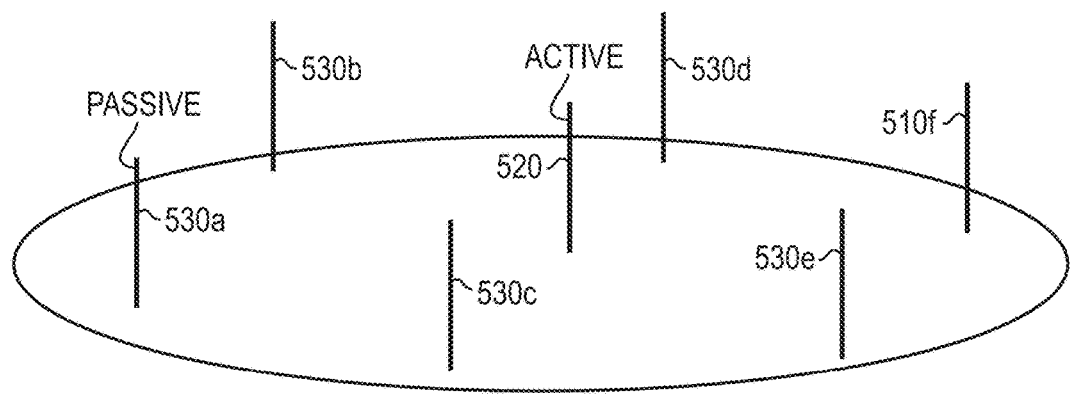
FIG. 5B is a simplified diagram of a steering antenna array.

FIG. 5B depicts a simplified diagram of a second embodiment of a steering antenna array 500b in which there is one active and multiple passive, inductively-coupled antennas. The steering antenna array 500b may be implemented in the system 400 as the steering antenna array 432. The steering array 500b includes at least one active antenna 520 and passive antennas 530a-530f. The steering antenna array 500b may be operated in a manner as is known in the art, and other embodiments of arrays with active and passive antenna elements may alternatively be used. Similarly, while steering antenna arrays 500a and 500b have been depicted, various other types of steering antenna arrays that are known in the art may alternatively be implemented in the system 400 as the steering antenna array 432.

The steering antenna array 500a or 500b has some advantages compared to the diversity antenna embodiment of FIG. 1. For example, the steering antenna array 500b has a single active antenna 520. Because there is only one active antenna 520 in the array 500b, only one receiver is needed for this array. An additional benefit of steering antenna arrays, such as arrays 500a and 500b, is the increased signal gain that these arrays provide compared to omnidirectional antenna elements of diversity antenna elements. The downside of these arrays however, may be increased complexity and expense. For example, the first embodiment of the steering antenna array 500a requires that each antenna 510a-510g be active, which requires an associated receiver for each antenna 510a-510g. Both steering antenna arrays 500a and 500b also include the increased complexity of a steering antenna array controller, such as the controller 440, which diversity antennas with standard receivers do not require.

Figure 6:
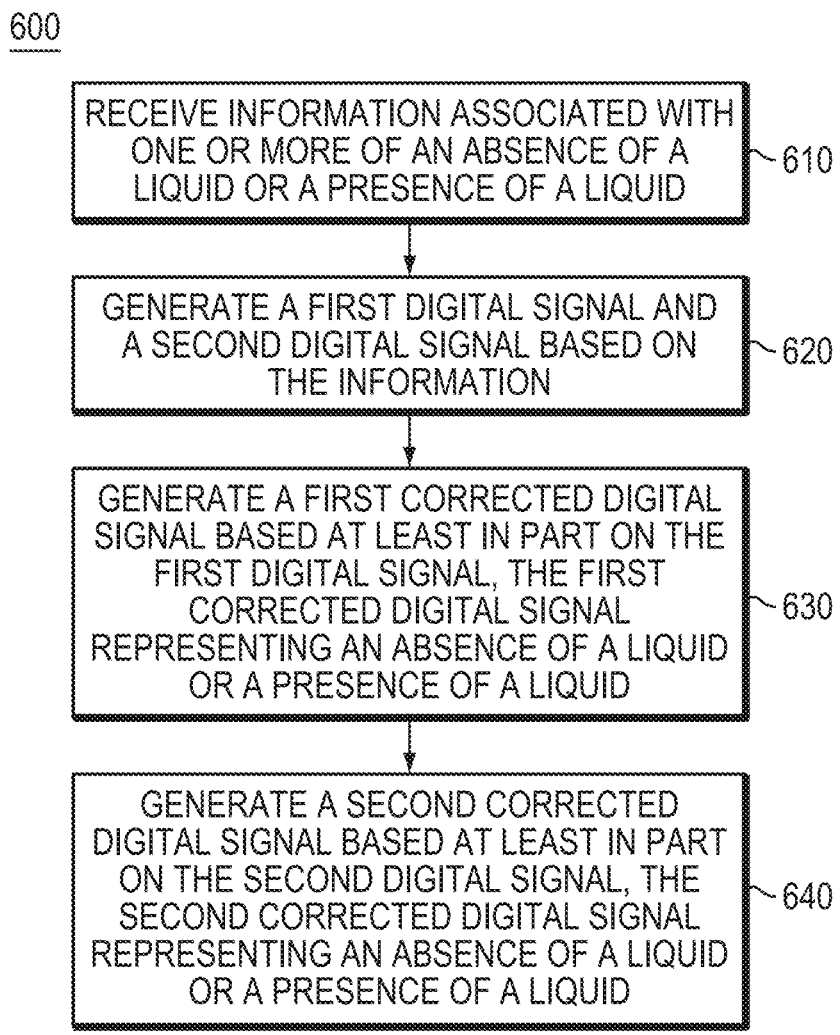
FIG. 6 is a flow chart of a method of monitoring blood leaks during hemodialysis therapy, according to at least one embodiment.

FIG. 6 depicts a flow chart of a method 600 for monitoring blood leaks during hemodialysis therapy, according to at least one embodiment. The method 600 begins by receiving information associated with either an absence or presence of a liquid (610). This information may be received from such sensors as WWDs 110, 710 or 1010. From the received information, a first digital signal and a second digital signal are generated (620). Next, using at least part of the first digital signal, a first corrected digital signal is generated (630). This first corrected digital signal may represent an absence of a liquid or a presence of a liquid. Finally, in a similar manner, a second corrected digital signal is calculated using, at least in part, the second digital signal (640).

The flow diagram of FIG. 6 may be modified for steering antenna embodiments to include control activity for tracking on a direct signal (i.e., choosing a best quality signal within a multi-path environment) and initial scanning activities to locate the direct signal and any multi-path signal(s) with sufficient signal quality. Other processes known in the art of steering antennas may also be employed. Reasons for tracking include changes in direction of a signal or reflection of a signal from the WWD due to patient movement or objects or persons obscuring a direct line of sight path between the WWD and steering antenna, as two examples.

Figure 7:
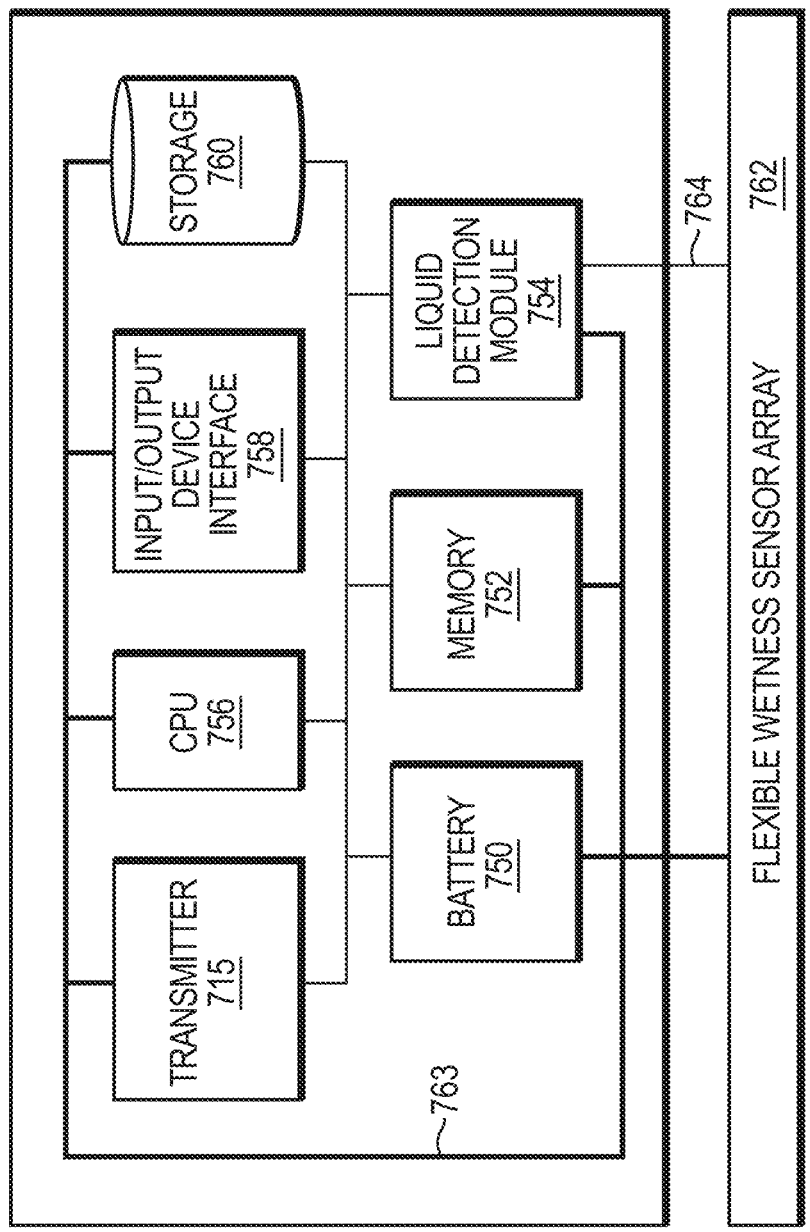
FIG. 7 illustrates a simplified block diagram of a flexible Wireless Wetness Detector (WWD) which may be implemented in an embodiment.

FIG. 7 is a high level block diagram of a WWD 710 which may be incorporated in an embodiment, such as the systems 100 or 300. The WWD contains an interconnect 759, which may be a bus, which serves as an interconnection between the various components of the WWD 710. Connected to the interconnect 759 is an input/output device interface 758 for connecting various input and output devices, such as a keyboard, mouse, display, speakers, etc. to the WWD 710. The WWD 710 further comprises a Central Processing Unit (CPU) 756. The CPU 756 provides for the execution of computer instructions. Memory 752 provides volatile storage for data used for carrying out computer instructions. Storage 760 provides non-volatile storage for software instructions. The WWD 710 further includes a battery 750. The battery 750 provides power for the various components of the WWD 710 via the power interconnect 763.

The WWD 710 further comprises a transmitter 715 for transmitting information from the WWD 710 to any device with an appropriate receiver, such as the wireless receiver 134 which is coupled to the hemodialysis machine 120. Further coupled to the WWD 710 is a liquid detection controller 754. The liquid detection controller 754 is configured to determine the presence or absence of a liquid based upon information from a flexible wetness sensor array 762, which may be integrated with or be a separately attachable component to the WWD 710. An alternative embodiment of the WWD 710 may use a non-flexible wetness sensor array.

The wetness sensor array 762 comprises a flexible conductive material that forms an electrical circuit through which wetness can be detected using conductivity of the liquid to which the electric circuit is exposed. This flexible wetness sensor 762 is configured to sit comfortably on a patient's person, such as on the patient's arm, torso, or leg. In an embodiment, the flexible wetness sensor array 762 is attached to a wound dressing and covers a needle insertion site. Through the flexible wetness sensor array 762 the WWD 710 can detect any liquid that is electrically conductive, i.e., contains positively and negatively charged ions that enable the liquid to carry electric current. The electric circuit can be resistive or capacitive so long as the presence of wetness results in a change in the resistance or capacitance of the circuit that is detectable by the liquid detection controller 754. For example, the circuit can be an open electric circuit, wherein the presence of moisture completes the circuit, thereby generating a change in the voltage or current of the circuit that can be detected by the liquid detection controller 754. A Wheatstone bridge is an example of a circuit that may be used to detect moisture, where one resistance path of the Wheatstone bridge is formed by the flexible wetness sensor array 762.

The flexible wetness sensor array 762 is connected to the liquid detection controller 754 via the interconnect 764. The exposure of the flexible wetness sensor array 762 to moisture leads to the generation of a detectable electric signal by the liquid detection controller 754. The liquid detection controller 754 receives this electric signal via the interconnect 764. The liquid detection controller 754 may further comprise an analog-to-digital (A-to-D) converter to digitize the electrical signal received from the flexible wetness sensor array 762. The liquid detection controller 754 is configured to evaluate a signal from the wetness sensor array 762 and determine the presence or absence of liquid. While the liquid detection controller 754 is configured to determine the presence or absence of a liquid, the liquid detection controller 754 may be configured to make this determination in accordance with a particular threshold. For example, the liquid detection module may only consider a change in the signal greater than a particular threshold as indicating the "presence of a liquid." This threshold may be determined and tuned by a person of skill in the art.

The liquid detection module 754 can send a signal to the transmitter 715 which indicates the presence or absence of a liquid based upon the liquid detection module's evaluation of a signal from the flexible wetness sensor array 762. The transmitter 715, can then, in turn, transmit this information to a hemodialysis machine, such as the hemodialysis machine 120, according to an embodiment. The frequency of transmissions indicating the presence or absence of liquid by the WWD 710 may vary depending upon the embodiment. For example, if information is being transmitted that indicates the presence of a liquid, this may be transmitted more frequently than information indicating the absence of a liquid. The frequency of transmissions may also vary depending upon operational factors such as power conservation.

In an embodiment, the WWD 710 comprises multiple transmitters. Such an embodiment provides transmitter redundancy which allows the WWD 710 to transmit information related to the presence or absence of a liquid even when there is a transmitter failure. In another embodiment with multiple transmitters, redundant transmitters that are not being utilized may be deactivated to help conserve power. In yet another embodiment, the transmitter 715 uses diversity antennas. The WWD 710 may receive feedback from a receiving system, such as the system 320, regarding which antennas to utilize. According to another embodiment, the transmitter 715 is coupled to a steering antenna array. In such an embodiment, a controller at the receiving system can send feedback to the WWD 710 to optimize the WWD's 710 steering antenna such that a pair of steering antennas on the WWD 710 and at the receiving system steer their respective beams toward each other, enabling the transmitter 715 to reduce its power due to high signal gain that results from the joint steering. Optimizing the steering antenna array may maximize the battery life of the WWD 710.

In an embodiment, the WWD 710 is configured to regulate the use of battery power. For example, if wetness is not detected for a specified period of time, the CPU 756 or the liquid detection controller 754 may direct components of the WWD 710 to enter low power modes. This may include, for example, lowering power to the flexible wetness sensor array 762, or halting non-essential functions of the CPU 756 or any of the components of the WWD 710.

Further detail regarding the operation of the WWD is given in U.S. Pat. No. 7,605,710 which is incorporated in its entirety by reference herein.

Figure 8:
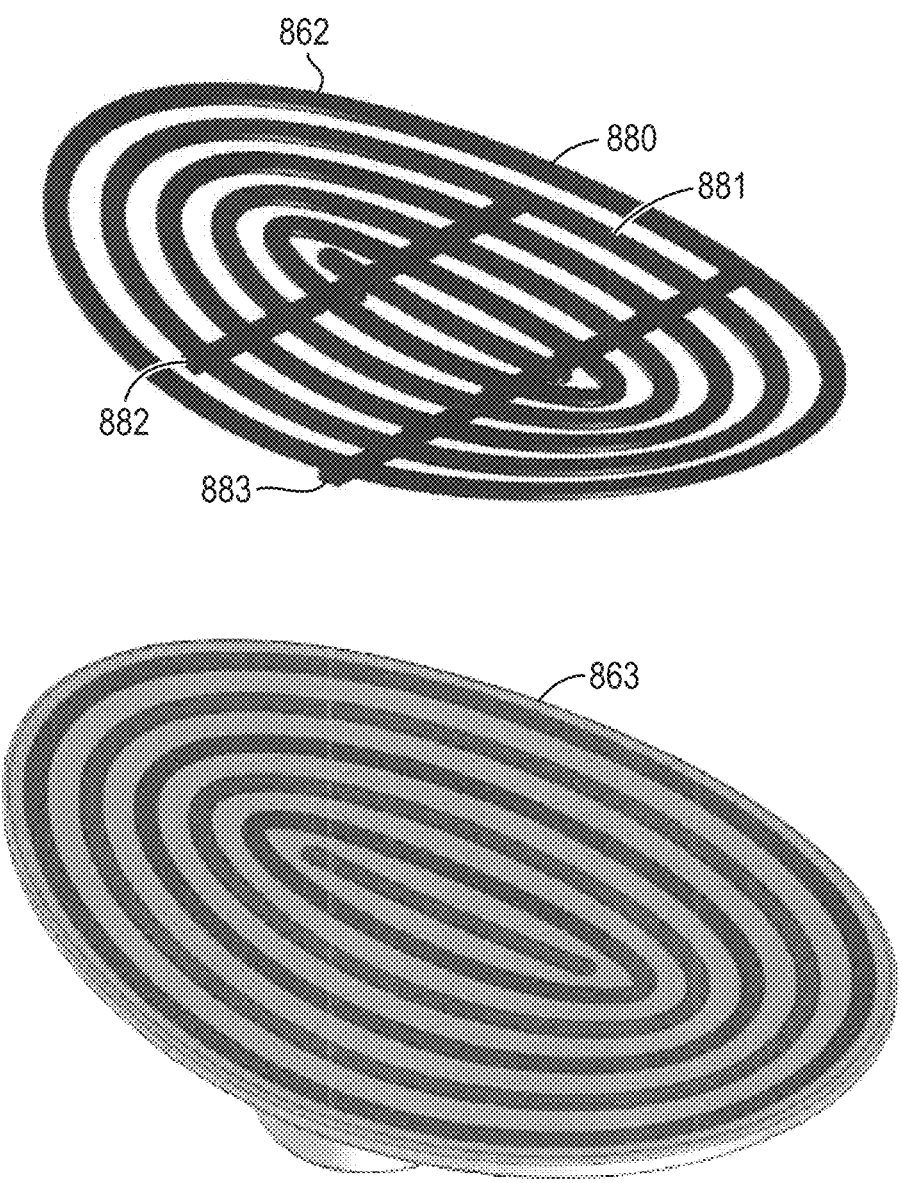
FIG. 8 depicts flexible wetness sensors that may be coupled to the WWD in embodiments.

FIG. 8 depicts a flexible wetness sensor array 862 that is coupled to the WWD in an embodiment. In an embodiment, the flexible conductive wetness sensor 862 is as described hereinabove as the flexible wetness sensor array 762. The flexible conductive sensor 862 is comprised of two conductive paths. The two conductive paths are made up of concentric rings, e.g., the rings 880 and 881. In an embodiment, the rings are powered in an alternating fashion via the connecting bars 882 and 880 respectively. The conductive sensor 862 may be made from any flexible conductive material that is known in the art, such as conductive Thermoplastic Polyurethane (TPU). In an embodiment the conductive sensor 862 is co-molded with non-conductive TPU to form an embodiment of the wetness sensor array 863.

Figure 9:
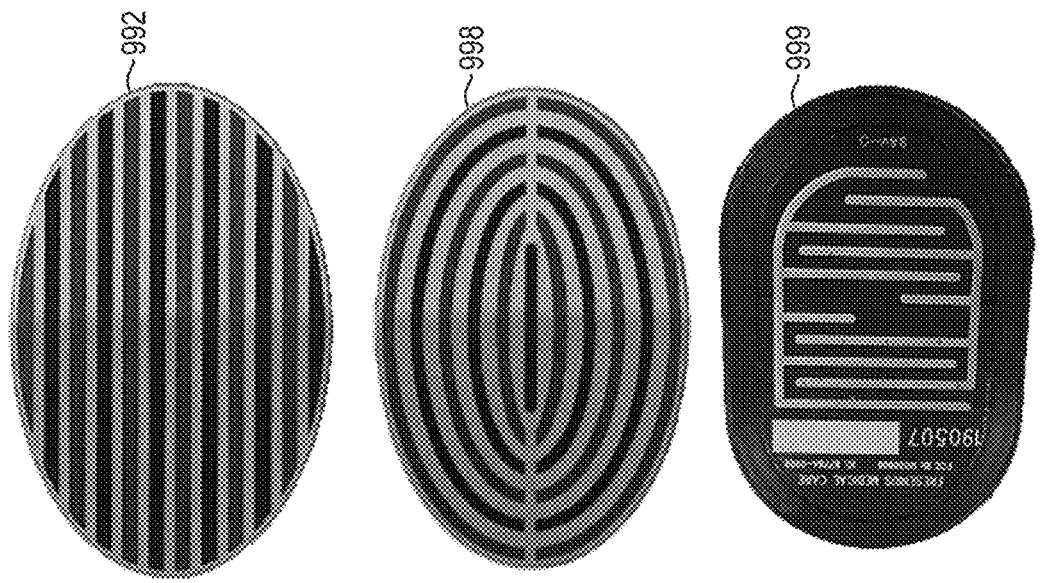
FIG. 9 depicts conductive sensor patterns that may be coupled to the WWD according to embodiments.
Figure 9:
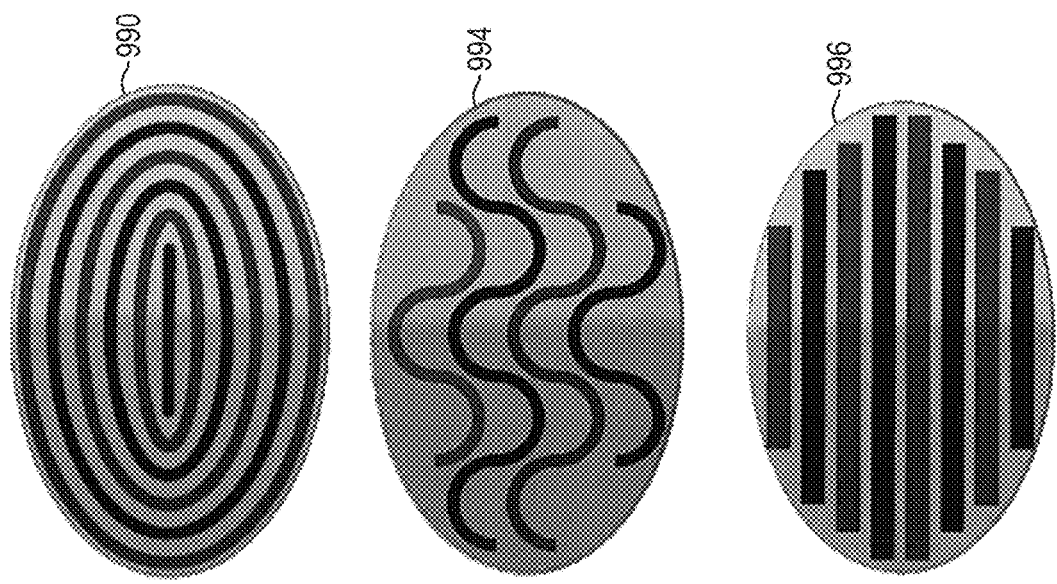

FIG. 9 depicts numerous conductive sensor patterns that may be incorporated into embodiments of the WWD. The numerous conductive patterns may be made using materials that are flexible and/or rigid and may be incorporated into WWDs that are flexible or rigid. The conductive patterns, 990, 992, 994, 996, 998, and 999 may be selected by a person of skill in the art based upon, for example, the application in which the sensor will be used. Further, the appropriate sensor pattern to utilize may also be determined based upon manufacturing characteristics such as cost and feasibility. In another embodiment, the sensor pattern is partitioned. Thus, the overall conductive pattern may comprise what are essentially multiple conductive sensor patterns. These multiple sensor patterns may be arranged in any manner known in the art. For example, each sensor pattern may comprise a quadrant of the wireless wetness sensor, thereby allowing the flexible WWD to detect the source of wetness based upon information from a particular quadrant of the sensor.

Figure 10:
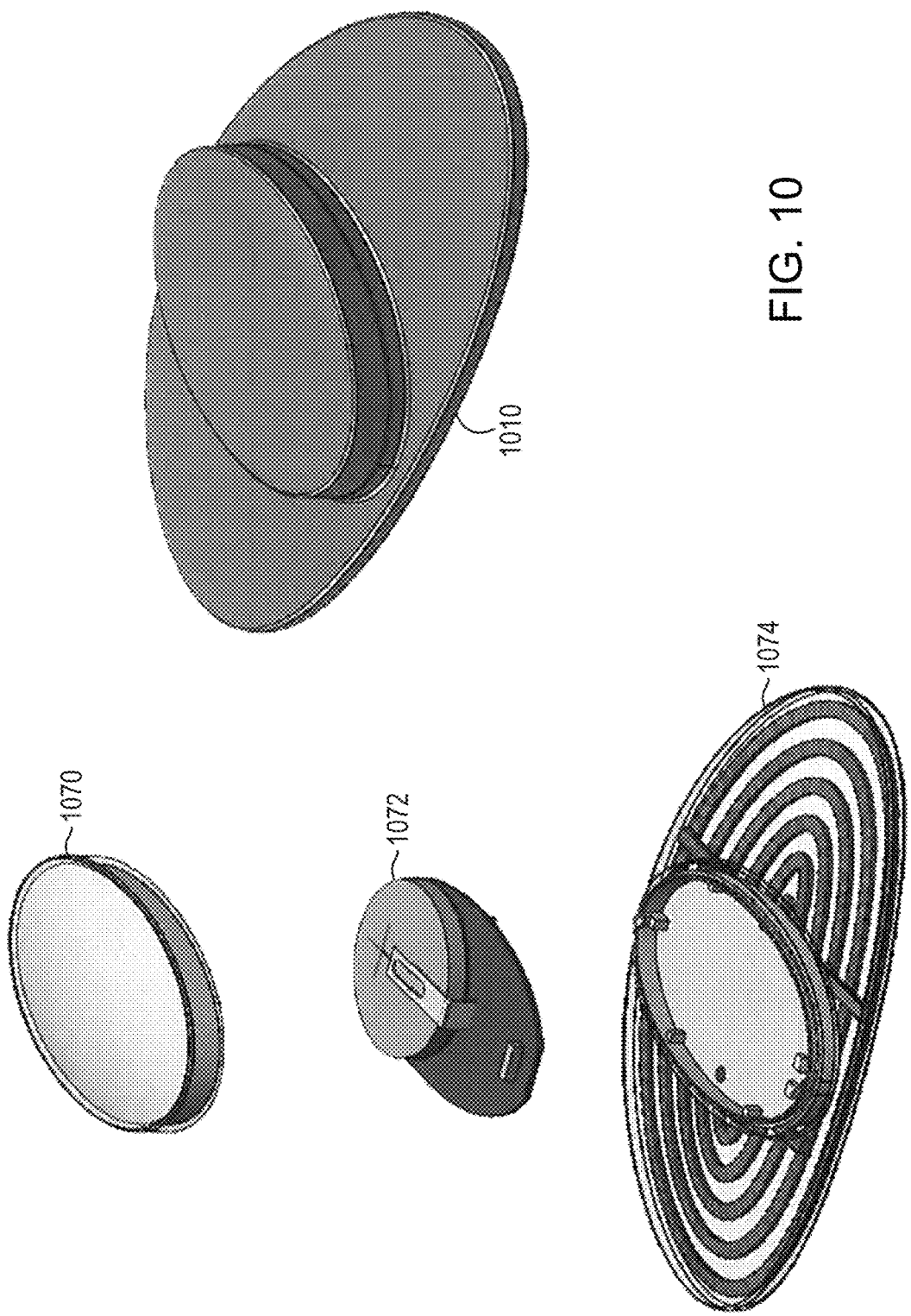
FIG. 10 depicts an exploded view and a completed view of a WWD according to an embodiment.

FIG. 10 illustrates exploded and completed views of a flexible WWD according to an embodiment. The flexible WWD 1010 is composed of a top cover assembly 1070, printed circuit board (PCB) assembly 1072, and main body assembly 1074.

Arranged on the bottom side of the main body assembly 1074 is a flexible wetness sensor array, such as the flexible wetness sensor array 762 or 862. According to an embodiment, the PCB assembly 1072 is mechanically and communicatively coupled to the top side of the main body assembly 1074. The PCB assembly 1072 comprises a liquid detection module, such as liquid detection module 754. The liquid detection module in the PCB assembly 1072 is configured to determine the presence or absence of a liquid based upon the effect the wetness sensor array on the bottom side on the main body assembly 1074 has on a circuit in the PCB assembly 1072. The PCB assembly 1072 further comprises a transmitter configured to transmit information associated with the determined presence or absence of liquid to a receiver, such as the receiver module 134 coupled to the hemodialysis machine 120. According to an embodiment, the PCB assembly 1072 comprises the components and operates in a manner as described hereinabove in relation to FIG. 7.

The WWD 1010 further includes a top cover assembly 1070. The top cover assembly 1070 is connected to the main body assembly 1074 to cover the PCB assembly 1072. When joined, the top cover assembly 1070, PCB assembly 1072, and main body assembly 1074, form the complete flexible WWD 1010. The top cover assembly and the main body assembly may be connected in any manner known in the art, including for example: mechanical coupling, ultrasonic welding, or solvent bonding. The top cover assembly 1070 and main body assembly 1074 may be composed of any material that is known in the art, including acrylonitrile butadiene styrene (ABS). In a further embodiment the top cover assembly 1070, PCB assembly 1072, and main body assembly 1074 are each made out of flexible materials known in the art.

It should be understood that the example embodiments described above may be implemented in many different ways. In some instances, the various methods and machines described herein may each be implemented by a physical, virtual or hybrid general purpose computer having a central processor, memory, disk or other mass storage, communication interface(s), input/output (I/O) device(s), and other peripherals. The general purpose computer is transformed into the machines that execute the methods described above, for example, by loading software instructions into a data processor, and then causing execution of the instructions to carry out the functions described, herein.

As is known in the art, such a computer may contain a system bus, where a bus is a set of hardware lines used for data transfer among the components of a computer or processing system. The bus or busses are essentially shared conduit(s) that connect different elements of the computer system, e.g., processor, disk storage, memory, input/output ports, network ports, etc., that enables the transfer of information between the elements. One or more central processor units are attached to the system bus and provide for the execution of computer instructions. Also attached to the system bus are typically I/O device interfaces for connecting various input and output devices, e.g., keyboard, mouse, displays, printers, speakers, etc., to the computer. Network interface(s) allow the computer to connect to various other devices attached to a network. Memory provides volatile storage for computer software instructions and data used to implement an embodiment. Disk or other mass storage provides non-volatile storage for computer software instructions and data used to implement, for example, the various procedures described herein.

Embodiments may therefore typically be implemented in hardware, firmware, software, or any combination thereof.

In certain embodiments, the procedures, devices, and processes described herein constitute a computer program product, including a non-transitory computer readable medium, e.g., a removable storage medium such as one or more DVD-ROM's, CD-ROM's, diskettes, tapes, etc., that provides at least a portion of the software instructions for the system. Such a computer program product can be installed by any suitable software installation procedure, as is well known in the art. In another embodiment, at least a portion of the software instructions may also be downloaded over a cable, communication and/or wireless connection.

Embodiments may also be implemented as instructions stored on a non-transitory machine-readable medium, which may be read and executed by one or more processors. A non-transient machine-readable medium may include any mechanism for storing or transmitting information in a form readable by a machine, e.g., a computing device. For example, a non-transient machine-readable medium may include read only memory (ROM); random access memory (RAM); magnetic disk storage media; optical storage media; flash memory devices; and others.

Further, firmware, software, routines, or instructions may be described herein as performing certain actions and/or functions of the data processors. However, it should be appreciated that such descriptions contained herein are merely for convenience and that such actions in fact result from computing devices, processors, controllers, or other devices executing the firmware, software, routines, instructions, etc.

It also should be understood that the flow diagrams, block diagrams, and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers, and/or some combination thereof, and, thus, the data processors described herein are intended for purposes of illustration only and not as a limitation of the embodiments.

While this invention has been particularly shown and described with references to example embodiments thereof, it will be understood by those skilled in the art that various changes in form and details may be made therein without departing from the scope of the invention encompassed by the appended claims.

What is claimed is:

1. A system comprising:
    a sensing device configured to wirelessly transmit information by a transmitter, the information associated with a presence or an absence of a condition occurring during a medical therapy; and
    a multi-antenna wireless receiver system comprising:
        a first antenna in communication with a first receiver and a second antenna in communication with a second receiver, the first antenna and the second antenna being configured to:
        wirelessly receive the information transmitted by the transmitter; and
    send the information to the first receiver and the second receiver, respectively;
    wherein the first receiver is configured to generate a first digital signal based on the information and the second receiver is configured to generate a second digital signal based on the information;
    a processor configured to:
    receive the first digital signal and the second digital signal;
    generate a first corrected digital signal based at least in part on the first digital signal, the first corrected signal representing the presence or the absence of the condition; and
    generate a second corrected digital signal based at least in part on the second digital signal, the second corrected signal representing the presence or the absence of the condition; and
    an operation unit that controls operation of a component of a medical therapy machine based on one or more of the first corrected digital signal and the second corrected digital signal.

2. The system of claim 1, wherein the condition is a wetness condition resulting from a leak during the medical therapy.

3. The system of claim 1, wherein the multi-antenna wireless receiver system is integrated into the medical therapy machine.

4. The system of claim 1, wherein the medical therapy machine is a dialysis machine and the operation unit controls operation of a pump of the dialysis machine.

5. The system of claim 1, wherein the processor continuously monitors data streams associated with the first antenna and the second antenna.

6. The system of claim 5, wherein the processor includes a decoder that uses a continuous monitoring window to process received data streams from one or more of the first receiver and the second receiver.

7. The system of claim 1, wherein the sensing device transmits information non-continuously.

8. The system of claim 7, wherein a time during which the sensing device transmits information is based on a data unit duration.

9. The system of claim 8, wherein the sensing device is transmitting for approximately 50% of the data unit duration.

10. The system of claim 1, wherein the processor is further configured to determine that one or more of the first corrected digital signal and the second corrected digital signal is authentic.

11. A method comprising:
receiving wirelessly information from a transmitter associated with a presence or an absence of a condition occurring during a medical therapy via at least two antenna elements;
generating a corresponding number of digital signals based on the information from the transmitter received via the at least two antenna elements; and
generating a respective number of corrected digital signals based at least in part on the digital signals, the corrected digital signals representing an absence of a liquid or a presence of a liquid and
controlling operation of a component of a medical therapy machine based on one or more of the corrected digital signals.

12. The method of claim 11, wherein the condition is a wetness condition resulting from a leak during the medical therapy.

13. The method of claim 11, wherein the multi-antenna wireless receiver system is integrated into the medical therapy machine.

14. The method of claim 11, wherein the medical therapy machine is a dialysis machine and the component being controlled is a pump of the dialysis machine.

15. The method of claim 11, further comprising:
continuously monitoring data streams associated with the at least two antenna elements.

16. The method of claim 15, further comprising:
using a continuous monitoring window to process received data streams from one or more of the first receiver or the second receiver.

17. The method of claim 11, further comprising:
transmitting wirelessly, from a sensing device, the information associated with the presence or the absence of the condition occurring during the medical therapy.

18. The method of claim 17, wherein the information is transmitted from the sensing device non-continuously.

19. The method of claim 18, wherein a time during which the wetness sensing device transmits information is based on a data unit duration.

20. The system of claim 19, wherein the wetness sensing device is transmitting for approximately 50% of the data unit duration.

21. The method of claim 11, further comprising:
determining that one or more of the corrected digital signals is authentic.

22. An apparatus comprising:
a first wireless receiving module comprising:
a first antenna coupled to a first receiver, the first antenna configured to receive information from a transmitter associated with one or more of a presence or an absence of a condition during a medical therapy, and the first receiver configured to generate a first digital signal based on the information;
a second wireless receiving module comprising:
a second antenna coupled to a second receiver, the second antenna configured to receive the information from the transmitter associated with one or more of the presence of the absence of the condition, and the second receiver configured to generate a second digital signal based on the information;
a processor configured to:
generate a first corrected digital signal based at least in part on the first digital signal, the first corrected digital signal representing the presence or the absence of the condition; and
generate a second corrected digital signal based at least in part on the second digital signal, the second corrected signal representing the presence or the absence of the condition; and
an operation unit that controls operation of a component of a medical therapy machine based on one or more of the first corrected digital signal or the second corrected digital signal.

23. The apparatus of claim 22, wherein the condition is a wetness condition resulting from a leak during the medical therapy.

24. The apparatus of claim 22, wherein the medical therapy machine is a dialysis machine and the operation unit controls operation of a pump of the dialysis machine.

25. The apparatus of claim 22, wherein the processor continuously monitors data streams associated with the first antenna and the second antenna.

26. The system of claim 25, wherein the processor includes a decoder that uses a continuous monitoring window to process received data streams from one or more of the first receiver or the second receiver.

27. The apparatus of claim 22, wherein the processor is further configured to determine that one or more of the first corrected digital signal and the second corrected digital signal is authentic.

* * * * *